United States Patent [19]

Hanna et al.

[11] Patent Number: 4,695,591

[45] Date of Patent: Sep. 22, 1987

[54] CONTROLLED RELEASE DOSAGE FORMS COMPRISING HYDROXYPROPYLMETHYLCELLULOSE

[75] Inventors: Gayda Hanna, Berwyn, Pa.; Winston A. Vadino, Bridgewater, N.J.

[73] Assignee: Schering Corporation, Kenilworth, N.J.

[21] Appl. No.: 801,130

[22] Filed: Nov. 22, 1985

Related U.S. Application Data

[63] Continuation-in-part of Ser. No. 718,036, Mar. 29, 1985.

[51] Int. Cl.⁴ .................. A61K 31/74; A61K 9/20; A61K 9/22
[52] U.S. Cl. .................. 514/781; 424/436; 424/488; 424/480; 424/493; 424/499
[58] Field of Search ............... 424/19, 22, 35; 514/781

[56] References Cited

U.S. PATENT DOCUMENTS

| | | | |
|---|---|---|---|
| 3,065,143 | 11/1962 | Christenson et al. | 424/35 |
| 3,870,790 | 3/1975 | Lowey et al. | 514/777 |
| 4,122,157 | 10/1978 | Huber | 424/19 |
| 4,140,755 | 2/1979 | Sheth et al. | 424/19 |
| 4,167,558 | 9/1979 | Sheth et al. | 424/19 |
| 4,226,849 | 10/1980 | Schor | 424/19 |
| 4,259,314 | 3/1981 | Lowey | 424/19 |
| 4,369,172 | 1/1983 | Schor et al. | 424/19 |
| 4,389,393 | 6/1983 | Schor et al. | 424/19 |
| 4,415,547 | 11/1983 | Yu et al. | 424/19 |
| 4,540,566 | 9/1985 | Davis et al. | 424/19 |
| 4,556,678 | 12/1985 | Hsiao | 514/652 |
| 4,571,333 | 2/1986 | Hsiao et al. | 424/19 |
| 4,601,894 | 7/1986 | Hanna et al. | 424/19 |

*Primary Examiner*—Shep K. Rose
*Attorney, Agent, or Firm*—Anita W. Magatti; Stephen I. Miller; James R. Nelson

[57] ABSTRACT

Controlled release solid dosage forms comprising less than about one-third of the total dosage form weight of hydroxypropylmethylcellulose USP 2910 are disclosed.

2 Claims, No Drawings

CONTROLLED RELEASE DOSAGE FORMS COMPRISING HYDROXYPROPYLMETHYLCELLULOSE

This application is a continuation-in-part of application Ser. No. 718,036, filed Mar. 29, 1985, now U.S. Pat. No. 4,601,894.

SUMMARY OF THE INVENTION

The present invention relates to controlled release solid dosage forms comprising a carrier base from which one or more therapeutically active medicaments may be slowly and regularly released upon administration.

The carrier base of the present invention, the hydroxypropylmethylcellulose known as METHOCEL E4M (trademark of The Dow Chemical Co.) and further identified as hydroxypropyl methylcellulose USP 2910 (HPMC USP 2910) comprises less than about one third of the weight of the unit dosage form and provides for release of the active ingredient(s) over a period of 2-14 hours.

BACKGROUND OF THE INVENTION

Controlled release dosage forms are well known, including solid dosage forms incorporating one or more active ingredients in addition to lubricants, carrier bases, fillers and other excipients, wherein the carrier base may be a hydrophillic, hydrophobic or water-insoluble polymer.

The mechanism by which controlled release dosage forms act to disperse the active ingredients over a period of time have been described at length in the literature. See for example, Manford Robinson, Chapter 14, "Sustained Action Dosage Forms", *The Theory and Practice of Industrial Pharmacy*, 2nd ed., ed. L. Lachman, H. Lieberman and J. Kanig (Philadelphia; Lea & Febiger, 1976). The various advantages of controlled release dosage forms are well known to those skilled in the art, e.g., the therapeutic advantages of sustained blood levels and better patient compliance, and the advantages of being able to use smaller dosage units and/or higher dosages per unit which make the dosage forms easier to administer and more economical to manufacture.

The use of HPMC 2910 has previously been disclosed, for example, by Christensen and Dale in U.S. Pat. No. 3,065,143, wherein at least one third of the weight of a controlled release tablet had to be HPMC USP 2910, and by Schor et al. in U.S. Pat. No. 4,389,393, wherein a hydroxypropylmethylcellulose having a methoxyl content of 16-24 weight-% and a number average molecular weight above 50,000 may be combined with HPMC USP 2910.

DETAILED DESCRIPTION OF THE INVENTION

The present invention relates to the use of HPMC USP 2910 as the sole carrier base in controlled release solid dosage forms wherein HPMC USP 2910 is present at about 1-30 weight-% of the total dosage form, preferably 1-12 weight-%, and more preferably 1-8 weight-%.

HPMC USP 2910, available from The Dow Chemical Co. as METHOCEL E4M, is a hydroxypropylmethylcellulose characterized by a 28-30 weight-% methoxyl content, a 7-12 weight-% hydroxypropyl content, and has a number average molecular weight of 93,000, and a viscosity in a 2% aqueous solution of 3500-5600 cps.

Solid dosage forms of this invention may be prepared for systemic administration of medicaments, e.g., by tablets or lozenges for oral delivery of drugs into the gastrointestinal tract, or for local administration, e.g., by tablets to be held in the mouth for oral absorbtion of the medication or by suppositories for rectal or vaginal administration of the medication.

One or more medicaments may be combined in a single dosage form, depending on the chemical compatibility of the combined active ingredients and the ability to obtain the desired release rate from the dosage form for each active ingredient. The determination of the effective amount of the medicament per dosage unit is easily determined by skilled clinicians.

Representative types of active medicaments include antacids, anti-inflammatory substances, coronary vasodilators, cerebral vasodilators, peripheral vasodilators, anti-infectives, psychotropics, antimanics, stimulants, antihistamines, laxatives, decongestants, vitamins, gastrointestinal sedatives, antidiarrheal preparations, antianginal drugs, vasodilators, antiarrythmics, antihypertensive drugs, vasoconstrictors and migraine treatments, anticoagulants and anti-thrombotic drugs, analgesics, anti-pyretics, hypnotics, sedatives, antiemetics, anti-nauseants, anticonvulsants, neuromuscular drugs, hyper- and hypoglycaemic agents, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucolytics, antiuricemic drugs, and other drugs or substances acting locally in the mouth, such as topical analgetics, local anaesthetics, etc.

Examples of specific active medicaments include aluminum hydroxide, prednisolone, dexamethasone, aspirin, acetaminophen, ibuprofen, isosorbide dinitrate, nicotinic acid, tetracycline, ampicillin, dexbrompheniramine, chlorpheniramine, albuterol, pseudoephdrine, loratadine theophylline, ascorbic acid, tocopherol, pyridoxine, metaclopramide, magnesium hydroxide, verapamil, procainamide hydrochloride, propranolol, captopril, ergotamine, fluazepam, diazepam, lithium carbonate, insulin, furosemide, hydrochlorthiazide, guaiphenesin, dextromethorphan and benzocaine, although any active medicament which is physically and chemically compatible with the hydroxypropylmethylcellulose carrier base and other tablet ingredients and which demonstrates the desired controlled release characteristics may be used in the present invention.

The dosage forms of the present invention also usually comprise one or more fillers and lubricating agents, and may comprise other excipients such as disintegrating agents, colorings and flavorings.

Typical fillers and lubricating agents are well known in the art, but for the present invention, preferred fillers are dibasic calcium phosphate and lactose and preferred lubricating agents are stearic acid and magnesium stearate. The concentrations of the fillers and lubricating agents are chosen in relation to the carrier base weight so that the resulting dosage forms have the appropriate size and degree of hardness, and will release the active ingredient(s) over the desired time period. For example, in tablets of this invention for oral systemic administration, fillers may be present at about 5-90% of the total dosage form weight, but are preferably present at 10–20% of the dosage form weight, and lubricating agents may be present at 0.1 to 5% of the total dosage form weight, but are preferably present at 0.5 to 2% of the dosage form weight.

The release rate of the active medicament(s) from the solid dosage forms of this invention may be adjusted to obtain the appropriate effect of the medication(s). For example, oral systemic dosage forms may be designed to release medication over various time ranges, e.g., 2–4 hours, 4–8 hours, 8–12 hours, or 12–14 hours, with 8–12 hours being preferred. Dosage forms for oral local administration are generally designed to release the medicament over a shorter time period, e.g., 15 minutes to 4 hours, but other locally administered dosage forms, e.g., suppositories, may be formulated to release the medicament(s) over a time range similar to oral systemic dosage forms.

The components of the solid dosage forms of the present invention are combined and formed into tablets by conventional means (see the examples). Solid dosage forms for oral systemic administration are preferably coated to facilitate swallowing and to preserve the integrity of the dosage form until it reaches the appropriate place in the gastrointestinal tract.

The following examples describe typical tablet formulations of the controlled release dosage forms of the present invention.

EXAMPLE 1

| Tablet Core | |
|---|---|
| Ingredients | mg/tab |
| Acetaminophen 90% | 555 |
| Pseudoephedrine Sulfate | 60 |
| Dicalcium Phosphate | 95 |
| Hydroxylpropyl Methylcellulose USP 2910 | 48 |
| Stearic Acid | 10 |
| Magnesium Stearate | 7 |
| | 775 |

EXAMPLE 2

| Tablet Core | |
|---|---|
| Ingredients | mg/tab |
| Albuterol Sulfate | 14.46 |
| Lactose | 333.54 |
| Hydroxypropyl Methylcellulose USP 2910 | 100 |
| Magnesium Stearate | 2 |
| | 450 |

EXAMPLE 3

| Tablet Core | |
|---|---|
| Ingredients | mg/tab |
| Acetaminophen 90% | 555.5 |
| Dicalcium Phosphate | 111.2 |
| Hydroxypropyl Methylcellulose USP 2910 | 45 |
| Stearic Acid | 9.3 |
| Magnesium Stearate | 3.5 |

| Tablet Core | |
|---|---|
| Ingredients | mg/tab |
| | 724.5 |

EXAMPLE 4

| Tablet Core | |
|---|---|
| Ingredients | mg/tab |
| Lithium Carbonate | 450 |
| Lactose | 95 |
| Hydroxypropyl Methylcellulose USP 2910 | 50 |
| Silica Gel | 2 |
| Magnesium Stearate | 3 |
| | 600 |

EXAMPLE 5

| Tablet Core | |
|---|---|
| Ingredients | mg/tab |
| Procainamide HCl | 500 |
| Lactose | 110 |
| Hydroxypropyl Methylcellulose USP 2910 | 30 |
| Stearic Acid | 8 |
| Magnesium Stearate | 2 |
| | 650 |

EXAMPLE 6

| Tablet Core | |
|---|---|
| Ingredients | mg/tab |
| Potassium Chloride | 600 |
| Dicalcium Phosphate | 70 |
| Hydroxypropyl Methylcellulose USP 2910 | 50 |
| Magnesium Stearate | 5 |
| | 725 |

Manufacture of Tablets

Blend all ingredients except lubricants (e.g., stearic acid, magnesium stearate) in a suitable mixer. Granulate the blended powders with water or a mixture of water and alcohol; a small portion of the hydroxypropyl methylcellulose may be dissolved in the water or water/alcohol mixture and used to granulate the powders if necessary. Dry the granules and mill if necessary. Blend the dried granules with the lubricants. Compress into millable size tablets. The tablets may be coated with standard coating agents using standard coating procedures if desired.

What is claimed is:

1. A controlled release dosage form comprising a combination of an analgesic-effective amount of acetaminophen, an anti-histaminic-effective amount of dexbrompheniramine maleate, a decongestive-effective amount of pseudoephedrine sulfate and hydroxypropyl methylcellulose U.S.P. 2910 as the carrier base, wherein said hydroxypropyl methylcellulose constitutes 4.6 to 12 weight-% of the total dosage form.

2. A dosage form of claim 1 wherein the hydroxypropyl methylcellulose constitutes 4.6 to 8 weight-% of the total dosage form.

* * * * *